(12) United States Patent
Hendriks

(10) Patent No.: US 8,842,208 B2
(45) Date of Patent: Sep. 23, 2014

(54) OPTICAL FIBER SCANNING PROBE

(75) Inventor: Bernardus Hendrikus Wilhelmus Hendriks, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 699 days.

(21) Appl. No.: 13/127,242

(22) PCT Filed: Nov. 9, 2009

(86) PCT No.: PCT/IB2009/054964
§ 371 (c)(1),
(2), (4) Date: May 3, 2011

(87) PCT Pub. No.: WO2010/055454
PCT Pub. Date: May 20, 2010

(65) Prior Publication Data
US 2011/0211104 A1  Sep. 1, 2011

(30) Foreign Application Priority Data
Nov. 14, 2008 (EP) .................... 08169088

(51) Int. Cl.
H04N 5/225 (2006.01)
G02B 26/10 (2006.01)
A61B 1/00 (2006.01)
A61B 1/07 (2006.01)
G02B 23/24 (2006.01)

(52) U.S. Cl.
CPC ........ G02B 23/2423 (2013.01); A61B 1/00172 (2013.01); A61B 1/07 (2013.01); A61B 1/00096 (2013.01); G02B 23/2469 (2013.01)
USPC ....................................... 348/335; 359/201.1

(58) Field of Classification Search
None
See application file for complete search history.

(56) References Cited

U.S. PATENT DOCUMENTS

| | | | | |
|---|---|---|---|---|
| 4,895,431 A | * | 1/1990 | Tsujiuchi et al. | 359/29 |
| 5,377,047 A | | 12/1994 | Broome et al. | |
| 5,494,483 A | * | 2/1996 | Adair | 600/111 |
| 5,603,687 A | * | 2/1997 | Hori et al. | 600/166 |
| 5,865,726 A | | 2/1999 | Katsurada et al. | |
| 7,033,317 B2 | | 4/2006 | Pruitt | |
| 8,537,203 B2 | * | 9/2013 | Seibel et al. | 348/45 |
| 2008/0221388 A1 | | 9/2008 | Seibel et al. | |

FOREIGN PATENT DOCUMENTS

| | | |
|---|---|---|
| EP | 1891885 A1 | 2/2008 |
| JP | 2004229963 | 8/2004 |
| WO | 0197902 A2 | 12/2001 |
| WO | 2005018441 A1 | 3/2005 |
| WO | 2007067163 A1 | 6/2007 |
| WO | 2008111970 A1 | 9/2008 |

* cited by examiner

Primary Examiner — Luong T Nguyen

(57) ABSTRACT

Optical probes are provided for miniature applications, e.g. medical inspections and procedures or in industrial inspections. The probe comprises an optical guide, a first lens system mounted on a distal end portion of the optical guide for focusing light from the optical guide, an actuator for displacing the distal end portion and the first lens system to enable optical scanning, and a second lens system fixed inside the probe to receive radiation from the first lens system. The second lens system is selected to enable a deflection of radiation from the first lens system in a direction corresponding to a direction of displacement of the first lens system by the actuator. The second lens system can be a cheap negative lens, and the invention is thereby particularly useful for increasing the field of view (FOV) of cheap, disposable optical probes.

13 Claims, 4 Drawing Sheets

OPTICAL FIBER SCANNING PROBE

FIELD OF THE INVENTION

The present invention relates to an optical probe suitable for miniature applications, e.g. in-vivo medical inspections and procedures or in industrial inspections, in particular a probe applying a confocal fiber-scanning endomicroscope. The invention also relates to a corresponding imaging system and a method for imaging with such an imaging system.

BACKGROUND OF THE INVENTION

For correct diagnosis of various diseases, e.g. cancer, biopsies are often taken. This can either be performed via a lumen of an endoscope or via needle biopsies. In order to find the correct position where the biopsy has to be taken, various imaging modalities are used such as X-ray, Magnetic Resonance Imaging (MRI) and ultrasound. For example in most of the cases of prostate cancer the biopsy is guided by ultrasound. Although helpful, these methods of guidance are far from optimal. The resolution is limited and, furthermore, these imaging modalities can in most cases not discriminate between benign and malignant tissue.

In order to relay visible images of the tissue to be scanned at the tip of the endoscope, biopsy needle or other miniaturized inspection devices, several systems have been employed: i) relay lens system, e.g. as in rigid endoscopes, ii) fiber bundle, e.g. in flexible endoscope, iii) camera sensor at the tip of the scanning device, e.g. in videoscopes or iv) fiber scanner located in front of a fixed lens system, e.g. in endomicroscopy.

Most of these systems, e.g. relay lens system and fiber bundles, involve complicated optics making these systems expensive and hence not suitable for production of disposable components. Also camera sensor in videoscope has the disadvantage that the image sensor must have a small lateral view, which makes these image sensors complicated and expensive as more common, and cheap technology, as in mobile phone cameras, cannot be applied. Finally, fiber scanners located in front of a fixed lens system have the disadvantage that in order to a have a reasonable field of view (FOV) a complicated lens system is required in combination with a rather large stroke of the fiber end as described for example in US2005/0052753.

Thus far, none of the above approaches seems to be a viable road towards an affordable disposable endoscope with a reasonable field of view.

In summary, previously disclosed fiber-scanning systems with a reasonable field of view (FOV) applies complex and expensive lens systems making them expensive and disadvantageous for use in disposable optical probes.

SUMMARY OF THE INVENTION

Hence, an improved optical probe would be advantageous, and in particular a less complicated and low cost optical probe providing a reasonable FOV would be advantageous.

In particular, it may be seen as an object of the present invention to provide an optical probe that solves the above-mentioned problems of the prior art with having a sufficient field of view and a simple and/or low cost lens system.

Thus, the above described object and several other objects are intended to be obtained in a first aspect of the invention by providing an optical probe, the probe comprising: i) a housing, ii) an optical guide with a distal end portion inside the housing, iii) a first lens system rigidly coupled to said distal end portion, iv) actuation means capable of displacing said distal end portion and the first lens system to enable optical scanning of a region of interest (ROI) at or beyond a distal end of the housing, and, v) a second lens system fixed inside a distal end portion of the housing to receive radiation from the first lens system.

The first lens system is selected to enable focusing of light from the optical guide at the region of interest, while the second lens system is selected to enable a further deflection of radiation from the first lens system in a direction corresponding to a direction of displacement of the first lens system by the actuation means. It should be mentioned, that the second lens system will also affect the focusing of the light, so that the position of the focal point from the focusing of the first lens system is moved due to the use of the second lens system.

The optical probe may be used to (1) illuminate the region of interest and/or to (2) form an image of the region of interest. From a ray-tracing point of view these usages are equivalent, and both are relied upon in the following description of the involved optics, without a description using one of the usages indicating a limitation to this usage. Hence the first lens system may serve to couple radiation from the optical guide and focus it at an object plane at the region of interest and/or collect radiation from such object plane and couple it into the optical guide. When the distal end of the guide and first lens system are displaced by the actuation means, then the radiation from the first lens system is deflected in that direction. The second lens system serves to further deflect the radiation to/from the first lens system, preferably in the same direction as the displacement of the first lens system. Hence, in the first use the second lens system serves to increase the illuminated area at the object plane. In the second use, the second lens system serves to increase the field of view (FOV) of radiation coupled to the optical guide by the first lens system.

In a second aspect, the present invention relates to a method for optical imaging, the method comprising:

providing an optical probe comprising a housing holding an optical guide with a distal end portion and a first lens system rigidly coupled to said distal end portion, illuminating a region of interest at a distal end of the optical probe;

receiving radiation from a part of the region of interest by the first lens system and coupling the received radiation to the optical guide;

displacing the first lens system to optically scan a region of interest;

deflecting radiation from said part of the region of interest system in a direction corresponding to a direction of displacement of the first lens system using a second lens system fixed inside a distal end portion of the housing.

In the following, a number of preferred and/or optional features, elements, examples and implementations will be summarized. Features or elements described in relation to one embodiment or aspect may be combined with or applied to the other embodiments or aspects where applicable. As an example, a feature or element described in relation to the optical probe may be implemented as a step in the method where appropriate. Also, explanations of underlying mechanisms of the invention as realized by the inventors are presented for explanatory purposes, and should not be used in ex post facto analysis for deducing the invention.

In an alternative formulation, the optical guide may define a centre axis of the scanning of the first lens system by the actuation means. The second lens system is selected to deflect radiation from the first lens system further away from the centre axis, when the first lens system is displaced away from the centre axis. In another alternative formulation, the second lens system is selected to deflect the focused radiation from the first lens system to increase the FOV.

The invention is particularly, but not exclusively, advantageous for increasing the FOV of an optical probe by deflecting the focused radiation from a lens system attached to an optical guide further away from the centre axis when the optical guide is displaced away from a centre axis or mid point of a scanning pattern.

In the context of the present invention it is to be understood that the term "optical guide" may include, and is not limited to, optical fibres (multi-mode and single-mode), thin film optical paths, photonic crystal fibres, photonic bandgab fibres (PBG), polarization maintaining fibres, and the like. The optical probe may also comprise more than one fibre i.e. a plurality of fibres or a fibre bundle.

Possibly when the optical guide is an optical fiber, the first lens system may be positioned at a distance (L) away from an optical exit of the optical fiber, the distance (L) being significantly larger than a core diameter ($d_f$) of the optical fiber. The ratio between the distance L and the optical fiber diameter at the exit position may be 0.5, 1, 5, 10, 20, 30, or higher.

Possibly the first lens system is rigidly connected to the optical guide with an intermediate mount fixated at the distal end portion of the optical guide and fixated on the first lens system.

In one embodiment in the optical probe according to the first aspect of the invention the second lens system is a negative lens or lens system with optical power $D_2$ ($=1/F_2$, where F designates the focal length) being negative (hence $F_2$ is also negative).

In another embodiment, the ratio of the absolute value of the optical power between the first and second lens systems is at least 25%, such as at least 26% or 30%.

In another embodiment of the invention the first lens system has an optical power $D_1$ ($=1/F_1$), and the ratio $D_2/D_1$ fulfill $D_2/D_1<0$ preferably $<-0.05$, $<-0.1<-0.2$ or $<-0.25$ or more preferably $<-0.30$.

The combined first and the second lens system form a total lens system with optical power $D_{tot}$. With the first and the second lens system separated by distance, d, the total optical power (or the focal length $F_{tot}$) can be approximated with the so called "thin lens approximation" by the relation $$\frac{1}{F_{tot}} = \frac{1}{F_1} + \frac{1}{F_2} - \frac{d}{F_1 F_2} = D_{tot}$$

In yet another embodiment of the invention, the second lens system is positioned a distance Q from an object plane of the probe, and Q, $D_1$, $D_2$ and d are selected so that $|QD_{tot}|>0.5$, preferably $>1$, $>5$, or $>10$. The object plane is the plane being imaged by the image system, also referred to as the region of interest (ROI), and is the focal plane of light from the optical guide through the total lens system. In a preferred embodiment, the object plane is the outer or distal surface of a window at the distal end of the probe.

The optical powers $D_1$ and $D_2$ and the distances L and d may be selected so that the focal point of the total lens system is formed at or outside of a distal end of the outer housing.

In a further embodiment the second lens system may comprise an aspherical lens, i.e. lenses where one or both surfaces have a shape that is neither spherical nor cylindrical. Possibly the first lens system may also comprises an aspherical lens.

Aspherical lenses have the advantage of producing images in which spherical aberration is eliminated and optical abberation is reduced when compared to images produced by simple lens. Therefore a single aspheric lens can often replace a much more complex multi-lens system. This provides the advantage of reducing the complexity of the lens design resulting in smaller, lighter and possibly cheaper system.

Possibly the second lens system is formed in polycarbonate. This provides the advantage of a cheap second lens system applicable in disposable probes. Other materials are for example but not limiting polymethylmethacrylaat (PMMA) or cyclo olefin copolymer (COC).

The probe according to first aspect preferably comprises a transparent window inside the housing at its distal end. In one embodiment, the second lens system forms the transparent window at a distal end of the housing, thereby saving the required material use for the probe and reducing fabrication steps—both of which may lead to a cheaper probe.

It should further be mentioned that the optical probe according to the present invention is particularly suited for relative simple and large-scale manufacturing because of the lens system being displaceably mounted on the end portion optical guide. From a practical point of view, the production of lens systems in polymer material, which are made by molding and therefore allowing mass production, may lower the unit-price per probe and therefore present a viable approach towards an affordable disposable endoscope. This is especially important because an endoscope, a catheter or needle with the optical probe embedded will normally be disposed after a single use due to sanitary requirements.

For some application the optical probe may form part of an endoscope, a catheter, a needle, or a biopsy needle, or other similar application as the skilled person will readily realize. It is also contemplated that fields of application of the present invention may include, but is not limited to, fields where small imaging devices are useful, such as in industries using inspection with small-scale devices etc.

Hence, in a third aspect, the present invention relates to an optical imaging system, the system comprising:

an optical probe according to the first aspect above, and
an imaging detector optically coupled to said optical probe for receiving radiation from a region of interest through the optical probe and forming an image.

Also, the method according to second aspect may further comprise performing an imaging process with an imaging detector optically coupled to said optical probe, the detector being arranged for imaging the region of interest.

In the context of the present invention it is to be understood that the term "radiation source" may comprise any suitable kind of radiation source including, and not limited to, lasers (of any wavelength and any mode of operation i.e. continuous or pulsed of any period incl. femto seconds laser), LEDs, gas-discharge lamps, any kind of luminescence, etc.

BRIEF DESCRIPTION OF THE FIGURES

The present invention will now be explained, by way of example only, with reference to the accompanying Figures, where.

DETAILED DESCRIPTION OF AN EMBODIMENT

Figure 1:
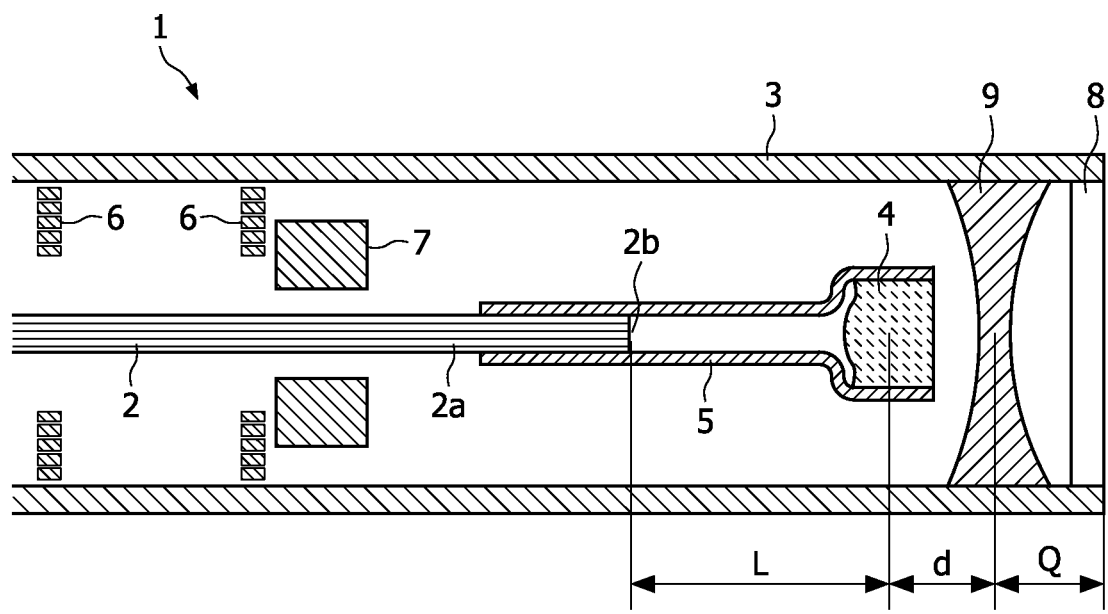
FIG. 1 is a schematic cross-sectional drawing of an optical scanning probe according to the present invention.

FIG. 1 shows a schematic cross-sectional drawing of an optical scanning probe according to the present invention. The optical probe 1 comprises an outer housing 3 holding an optical guide 2 with a first lens system 4 fastened at its distal end, preferably in a mechanical manner such as by an intermediate mount 5. The mount 5 holds the position of the distal end portion 2a of the optical guide 2 and the first lens system 4 in a fixed position relatively to each other by keeping the first lens system 4 centered on the longitudinal axis of the optical guide 2. The distance L between the optical exit 2b of the optical guide 2 and the first lens system 4 is typically significantly larger than a core diameter ($d_f$) of the optical guide 2.

The first lens system 4, which is rigidly coupled to the distal end portion of the optical guide 2a focus light coupled out from the optical guide 2. In FIG. 1, the first lens system is shown as a single lens for reason of clarity. The first lens system 4 is preferably an aspheric lens and may also have more than one lens and also may contain diffractive elements or mirror elements.

The distal end 2a and the first lens system 4 can be displaced by use of actuation means. When the actuation means are off, or set in what is to be a center position in the scanning motion of the distal end 2a and the first lens system 4, the longitudinal axis of the optical guide 2 defines a center axis or a midpoint of a scanning pattern. The displacement of the distal end 2a and first lens system 4 during scanning can thereby be described as displacements away from this center axis, and occurs through a deflection or bending of the optical guide 2 away from its position at the center axis.

When the first lens system 4 is on the center axis (not displaced), radiation from the optical guide will be focused on the center axis by the first lens system. Displacing the first lens system 4 away from the center axis means that radiation from the optical guide will be directed away from the center axis, and successive displacement in a scanning pattern generates the field of view (FOV).

In the embodiment illustrated in FIG. 1, the actuation means is an electro mechanic motor system with coils 6 and magnets 7. The coils can be attached in the housing and the magnets can be attached to the distal end 2a of the optical guide 2, or could be attached to the intermediate mount 5. Controlling a current through coils 6 can deflect the distal end 2a and first lens system 4 away from the center axis. Typically, the center axis will correspond to the position of the optical guide when no current through coils 6, its relaxed position, and the optical guide 2 thereby acts as spring element.

The housing 3 can have, at its distal or sampling end, a transparent exit window 8 for sealing the housing. The exit window 8 can be a plane section of an optical transport glass or polymer. The probe is normally held so that the window 8 touches the tissue to be imaged (ROI), whereby the outer or distal surface of a window forms the object plane of the probe.

A second lens system (9) is fixed inside the distal end portion of the housing, distal to the first lens system in order to receive radiation from the first lens system. The distance between the first and the second lens system is d. In one embodiment, the second lens system is positioned between the exit window 8 and the first lens system 4. In an alternative embodiment, the second lens system itself forms the transparent window. The distance between the second lens system and the object plane is called Q.

The second lens system 9 can be a negative or diverging lens, preferably with a center of symmetry on the center axis of the optical guide 2 or midpoint of the scanning pattern. The second lens system 9 provides the function of deflecting the radiation from the first lens system 4 further away from the center axis when the first lens system is displaced away from the center axis. Thus when a beam of light leaving the first lens system passes through the second lens system it diverges and appears to be originated from a particular point on the center axis. The second lens system thereby increases the FOV generated by the scanning of the first lens system, and thereby increases the FOV of the probe, without introducing added complexity or movable parts in the probe.

Examples of negative lenses are biconcave or plano-concave lens and may be made of glass, resins of different polymer materials, e.g. polycarbonate, polymethylmethacrylaat (PMMA) or cyclo olefin copolymer (COC).

Figure 2A:
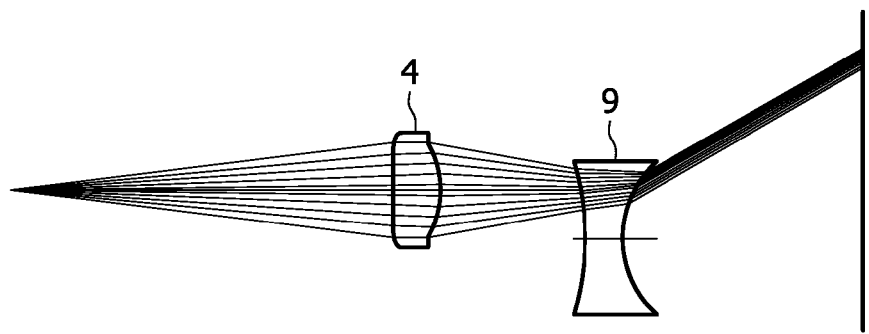
FIGS. 2a, 2b and 2c are the different optical path of a light beam leaving the optical guide for an optical probe according to the present invention when the optical guide is displaced in three different positions.
Figure 2B:
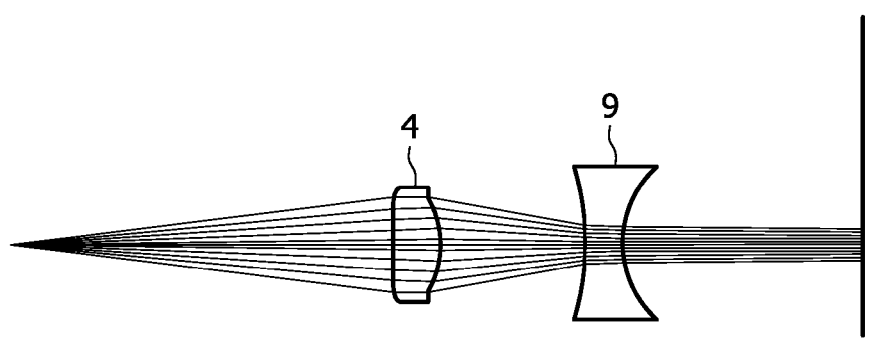
Figure 2C:
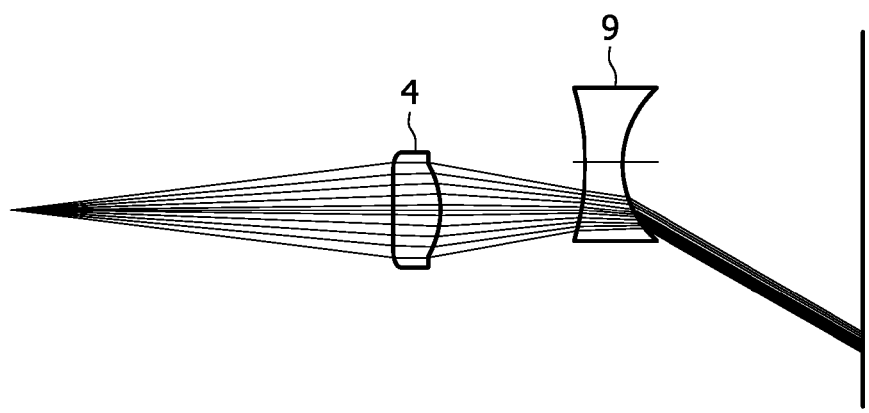

FIGS. 2a-c show ray-trace plot of trajectories for different positions of the optical guide 2 with the first lens system 4 attached to it, with the second lens system 9 fixed in relation to the housing (not shown).

FIG. 2a shows the optical path of a light beam leaving the optical guide when the first lens system 4 coupled to the optical guide 2 is displaced sideways away from the centre axis and towards one side of the housing 3. Following the displacement of the optical guide 2, the light beam is in turn displaced and hits the second lens system 9, i.e. a negative or diverging lens in a position away from the centre axis and towards one side of the housing 3. Thus The light beam passing through the second lens system 9 is spread and diverges away from the centre axis outside the optical probe 1.

FIG. 2b shows the optical path of a light beam leaving the optical guide in absence of any displacement, when the first lens system 4 coupled to the optical guide 2 is centered on the centre axis. It can be seen, that as the first lens system is not displaced, there is no further deflection from the second lens system.

FIG. 2c shows the optical path of a light beam leaving the optical guide when the first lens system 4 coupled to the optical guide 2 is displaced sideways away from the centre axis and towards a side of the housing 3 which is opposite to the one shown in FIG. 2a.

An exemplary embodiment will now be described in relation to FIG. 1. In this embodiment, the first lens system (4) consists of an aspherical lens made of PMMA attached to an optical fiber (2). The stop is on this lens on the side facing the ROI. Some of the properties of the first lens system in this embodiment are:

Stop diameter=2 mm
Focal length $F_1$=3.329 mm
Material: PMMA
Shape: bi-asphere

In the exemplary embodiment, the second lens system (9) is made of Polycarbonate because of a higher refractive index (give rise to a lower curvature of the surfaces) and is also apsherical. Some of the properties of the second lens system in this embodiment are:

Diameter=3.2 mm
Focal length $F_2$=−2.265 mm
Material: Polycarbonate
Shape: bi-asphere
Distance between second lens system and object plane Q=40.0 mm With these selections of the first and second lens systems, some of the properties of the total lens system in this embodiment are:

FOV=60 degrees

F#=4.0

Focal length $F_{tot}$=3.414 mm

Required stroke fiber=−1 mm to +1 mm

For this system we find $D_2/D_1=F_1/F_2$=−1.47, $D_2/D_{tot}=F_{tot}/F_2$=−1.51 and $|QD_{tot}|$=11.72.

Figure 3:
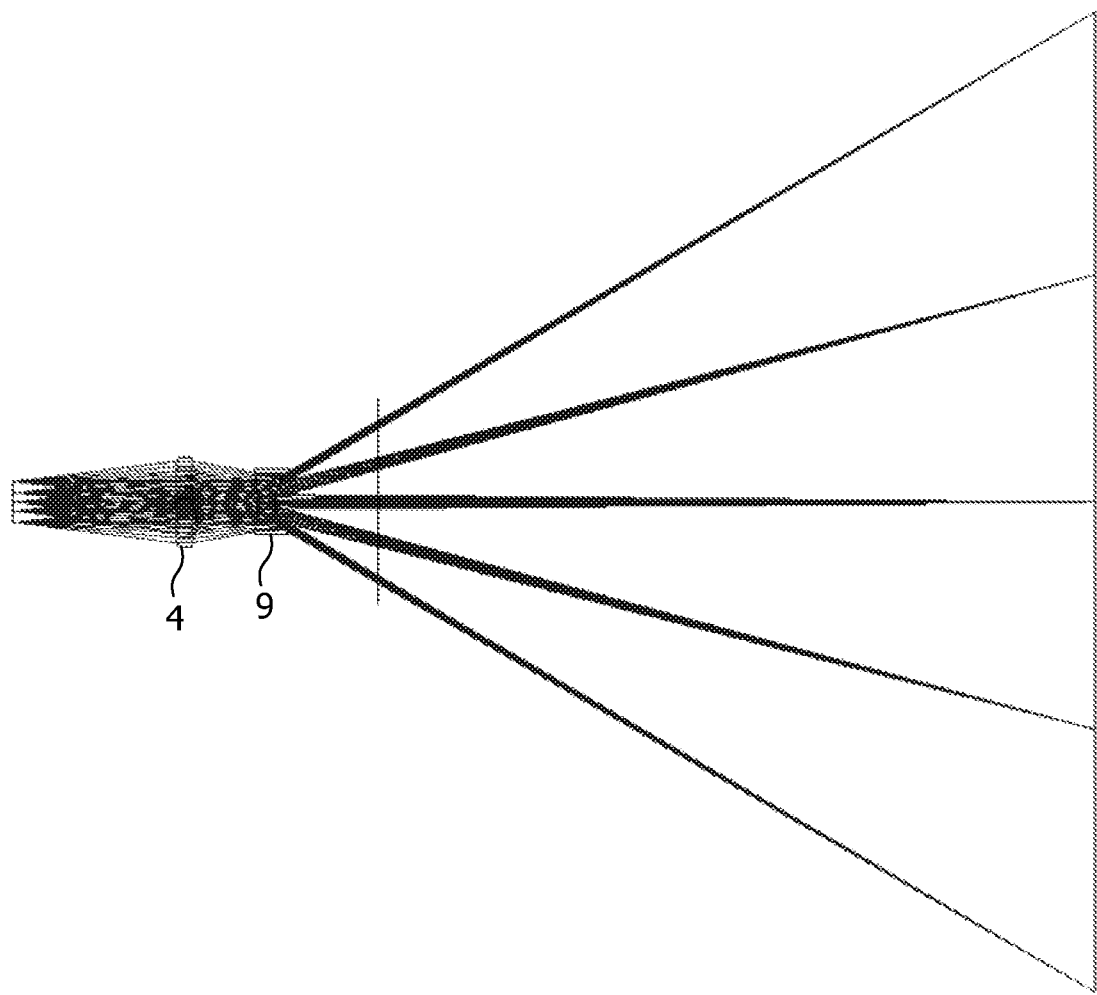
FIG. 3 shows the FOV, which may be achieved by scanning a region of interest (ROI) with an optical probe according to the present invention.

FIG. 3 shows Ray-trace plot of the possible optical paths defined by the different displacement of the first lens system 4 coupled to the optical guide 2 and thereby illustrates the increase in FOV created by the second lens system. The combination of the possible displacement induced by the actuation means defines the FOV that may be achieved by scanning a ROI with an optical probe according to the present invention.

Figure 4:
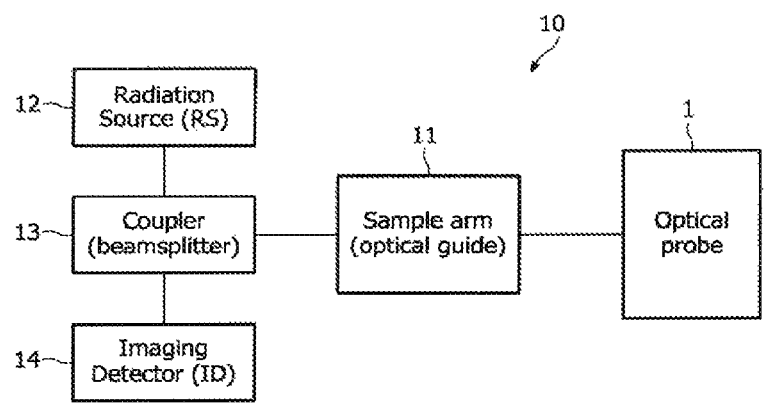
FIG. 4 is a schematic drawing of an optical imaging system according to the present invention.

FIG. 4 is a schematic drawing of an optical imaging system 10 according to the present invention. The optical imaging system comprises an optical probe 1 as described above, the optical probe located at the end of a sample arm 11. The sample arm 11 is preferably an optical guide with high degree of flexibility and bend-ability.

The region of interest to be imaged may be illuminated by the probe or by other lightning, e.g. a fixed optical guide that is not scanned. Preferably, a radiation source (RS) 12 can be optically coupled to the optical probe 1 via a coupler 13 to illuminate the region to be imaged. The coupler or beam splitter 13, e.g. a grating or a partial mirror, has the function of partially transmit the incoming beam from the RS and partially reflect the returning light beam from the ROI directing it towards the imaging detector (ID) 14. The probe 1 is accordingly arranged for guiding radiation, e.g. laser light, emitted from the radiation source 12 to a region of interest. Furthermore the ID 14 is optically coupled to the optical probe 1. The ID is arranged for imaging using reflected or emitted radiation from the region of interest in the sample (not shown) which reaches the ID 14 after being reflected by the coupler 13. The imaging detector 14 may also comprise a user interface (UI) so accessing results and/or controlling the imaging process (not shown).

Figure 5:
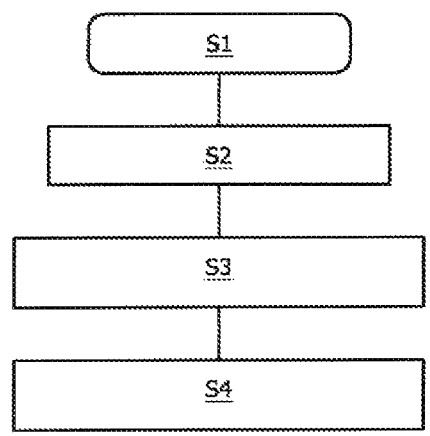
FIG. 5 is a flow chart for a method according to the invention.

FIG. 5 is a flow chart for an embodiment of a method according to the invention. The method comprises the following steps: S1, providing an optical probe as described in relating to FIG. 2, S2, coupling radiation from a radiation source (RS) to the optical guide 2 of the probe 1, and focusing radiation emitted from the optical guide by the first lens system (4), S3, displacing the first lens system to optically scan a region of interest (ROI), and S4, deflecting radiation from the first lens system in a direction corresponding to a direction of displacement of the first lens system using a second lens system (9) fixed inside a distal end portion of the housing.

The individual elements of an embodiment of the invention may be physically, functionally and logically implemented in any suitable way such as in a single unit, in a plurality of units or as part of separate functional units. The invention may be implemented in a single unit, or be both physically and functionally distributed between different units and processors.

Although the present invention has been described in connection with the specified embodiments, it is not intended to be limited to the specific form set forth herein. Rather, the scope of the present invention is limited only by the accompanying claims. In the claims, the term "comprising" does not exclude the presence of other elements or steps. Additionally, although individual features may be included in different claims, these may possibly be advantageously combined, and the inclusion in different claims does not imply that a combination of features is not feasible and/or advantageous. In addition, singular references do not exclude a plurality. Thus, references to "a", "an", "first", "second" etc. do not preclude a plurality. Furthermore, reference signs in the claims shall not be construed as limiting the scope.

The invention claimed is:

1. A scanning optical probe (1) comprising:

a housing (3), an optical guide (2) with a distal end portion (2a) inside the housing, a first lens system (4) rigidly coupled to said distal end portion, actuation means (6, 7) capable of displacing said distal end portion and the first lens system to enable optical scanning of a region of interest (ROI) at a distal end of the housing, and a second lens system (9) fixed inside the distal end of the housing to receive radiation from the first lens system, wherein the first lens system is selected to enable focusing of light from the optical guide at the region of interest, and wherein the second lens system is selected to enable a deflection of the focused light from the first lens system in a direction corresponding to a direction of displacement of the first lens system by the actuation means.

2. The scanning optical probe according to claim 1, wherein the optical guide defines a center axis of the scanning of the first lens system displaced by the actuation means, and wherein the second lens system is selected to deflect the focused light from the first lens system further away from the center axis, when the first lens system is displaced away from the center axis.

3. The scanning optical probe according to claim 1, wherein the second lens system is a negative lens system with optical power $D_2$<0.

4. The scanning optical probe according to claim 3, wherein the first lens system has an optical power $D_1$, and wherein a ratio $D_2/D_1$ fulfill $D_2/D_1$<0.1.

5. The scanning optical probe according to claim 4, wherein $D_2/D_1$<−0.25.

6. The scanning optical probe according to claim 1, wherein the combined first and the second lens system has an optical power $D_{tot}$ and the second lens system is positioned a distance Q from an object plane of the probe, and wherein $|QD_{tot}|$>0.5.

7. The scanning optical probe according to claim 1, wherein the second lens system (9) comprises an aspherical lens.

8. The scanning optical probe according to claim 1, wherein the second lens system (9) is formed in polycarbonate.

9. The scanning optical probe according to claim 1, wherein the second lens system (9) is a biconcave lens.

10. The scanning optical probe according to claim 1, wherein the second lens system also forms a transparent window (8) at the distal end of the housing.

11. The scanning optical probe according to claim 1, wherein the housing (3) comprises at its distal end a transparent window (8), the transparent window having an insignificant optical power as compared to the optical power of the first (4) and second lens systems (9).

12. The scanning optical probe according to claim 1, wherein the probe forms part of an endoscope, a catheter, a needle, or a biopsy needle.

13. An optical imaging system (100), the system comprising the scanning optical probe (1) according to claim 1, and an imaging detector (ID) optically coupled to said optical probe (1) for receiving radiation from a region of interest through the optical probe and forming an image.

\* \* \* \* \*